United States Patent [19]

Brazdil et al.

[11] Patent Number: 5,079,207
[45] Date of Patent: Jan. 7, 1992

[54] CATALYST FOR AMMOXIDATION OF PARAFFINS

[75] Inventors: James F. Brazdil, Mayfield Village; Linda C. Glaeser, Lyndhurst; Mark A. Toft, Lakewood, all of Ohio

[73] Assignee: The Standard Oil Company, Cleveland, Ohio

[21] Appl. No.: 620,814

[22] Filed: Dec. 3, 1990

[51] Int. Cl.$^5$ .................. B01J 23/14; B01J 23/18; B01J 23/22; B01J 23/32; B01J 23/72
[52] U.S. Cl. .................. 502/205; 502/206; 502/209; 502/215; 502/303; 502/304; 502/312; 502/325; 502/331; 502/340; 502/343; 502/345; 558/322; 558/324; 558/325
[58] Field of Search ........... 502/205, 206, 209, 215, 502/345, 303, 304, 312, 325, 331, 340, 343; 558/322, 324, 325

[56] References Cited

U.S. PATENT DOCUMENTS

| | | | |
|---|---|---|---|
| 4,316,855 | 2/1982 | Grasselli et al. | 502/215 |
| 4,339,394 | 7/1982 | Grasselli et al. | 502/215 X |
| 4,532,083 | 7/1985 | Suresh et al. | 423/508 X |

OTHER PUBLICATIONS

Above References A and C were cited by Applicants.

*Primary Examiner*—W. J. Shine
*Attorney, Agent, or Firm*—C. S. Lynch; M. F. Esposito; L. W. Evans

[57] ABSTRACT

Disclosed is a process for making an $\alpha$, $\beta$-unsaturated monoitrile by the catalytic reaction of a paraffin containing 3–5 carbon atoms with molecular oxygen and ammonia by catalytic contact of the foregoing reactants in a reaction zone with a metal oxide catalyst containing the elements indicated by the empirical formula, $$V_v A_a D_d Sn_m Sb_n Cu_c O_x \qquad \text{(formula 1)}$$

in the relative atomic proportions indicated by the subscripts, where

A is selected from Te and Bi
D is one or more optional elements selected from Mo, W, Ti, Ge, Ce, La, Cr, Mn, Mg, Ca, Co, Ni, Fe, Nb, Ta, Ag, Zn, Cd, B, P, Na, K and Cs, and
a is 0.001 to 30
d is zero to 30
c is 0.001 to 30
m is 0.1 to 60
n is 0.1 to 60
n/v is > 12 and < 100
m+n is $\geq$ v+a+c+d, and
x is determined by the valence requirements of the elements present, and wherein the reactants fed to the reaction zone contain a mole ratio of said paraffin:$NH_3$ in the range from 2 to 16 and a mole ratio of said paraffin:$O_2$ in the range from 1 to 10.

1 Claim, No Drawings

CATALYST FOR AMMOXIDATION OF PARAFFINS

This invention relates to an improved process for the catalytic ammoxidation of paraffins containing from 3 to 5 carbon atoms to α,β-unsaturated mononitriles, especially paraffins containing 3 to 4 carbon atoms. Most important is the ammoxidation of isobutane to methacrylonitrile and, especially, of propane to acrylonitrile.

Because of the price differential between propylene and propane an economic incentive exists for the development of a viable catalytic process for conversion of propane to acrylonitrile.

Early attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated mononitriles and the corresponding mono-olefins.

Still another object is to provide an improved catalyst for making unsaturated mononitriles from lower paraffins.

Other objects, as well as aspects, features and advantages, of the present invention will become apparent from a study of the accompanying disclosure and the claims.

These and other objects are achieved by the present invention according to one aspect of which there is provided a process for making an α,β-unsaturated mononitrile by the catalytic reaction of a paraffin containing 3–5 carbon atoms with molecular oxygen and ammonia by catalytic contact of the foregoing reactants in a reaction zone with a metal oxide catalyst containing the elements indicated by the empirical formula, $$V_v A_a D_d Sn_m Sb_n Cu_c O_x \qquad \text{(formula 1)}$$

in the relative atomic proportions indicated by the subscripts,
where
A is selected from Te and Bi
D is one or more optional elements selected from Mo, W, Ti, Ge, Ce, La, Cr, Mn, Mg, Ca, Co, Ni, Fe, Nb, Ta, Ag, Zn, Cd, B, P, Na, K and Cs, and
a is 0.001 to 30
d is zero to 30
c is 0.001 to 30
m is 0.1 to 60
n is 0.1 to 60
n/v is >12 and <100
m+n is ≧v+a+c+d, and
x is determined by the valence requirements of the elements present, and
wherein the reactants fed to the reaction zone contain a mole ratio of said paraffin:NH$_3$ in the range from 2 to 16 and a mole ratio of said paraffin:O$_2$ in the range from 1 to 10.

U.S. Pat. Nos. 4,316,855 and 4,532,083 disclose the ammoxidation of olefins in the presence of a catalyst containing Sb, Sn, and Te and that can contain Cu, V, W, Mo, Bi, Ti, Ge, La, Cr, Mn, Mg, Ca, Co, Ni, Nb, Ta, Ag, Zn, Cd, K, Cs, B, P, En. Neither V nor Cu is a necessary element.

The process of the present invention requires no halogen or halogen compounds and no sulfur or sulfur compounds in any form in the reaction zone, from either the feed to the reaction zone or in the catalyst composition.

In the catalyst compositions of the invention the empirical formula denotes the atomic ratios of the listed elements and does not, of course, connote any particular chemical compound, nor indicate whether the elements are present as a mixture of individual oxides or as a complex oxide or oxides, or what separate crystalline phases or solid solutions may be present. However, the catalyst contains the elements and proportions indicated by the foregoing formula. Similarly, the designation of certain oxides, such as "silica" or "alumina" or SiO$_2$ or Al$_2$O$_3$, as supports or diluents is merely in accordance with convention in the inorganic oxide catalyst art, and such designations refer to compounds often regarded as supports or carriers in the catalyst art. Such designations, however, do not mean that the element involved is actually present as a simple oxide. Indeed, such elements may at times be present as a complex oxide with one, more than one, or all of the elements in the foregoing empirical formula, which complex oxides form during the process for preparing the catalyst composition.

In the ammoxidation of the present invention, the reaction is carried out in the gas phase by contacting a mixture containing the paraffin, ammonia and molecular oxygen, and diluent, if any, conveniently in a fixed bed of the catalyst, or a gravity flowing bed, a fluidized bed or a fast transport reactor mode.

The mole ratio of O$_2$ to NH$_3$ fed to the reaction zone is usually in the range from 1–10 (more often 1–5), and the mole ratio of gaseous diluent (other than C$_3$ to C$_5$ paraffin) to paraffin is usually in the range from zero–20 (more often zero–12); of course, even higher molar ratios, say up to 50 mols diluent to 1 mols paraffin, can be used but are usually uneconomical.

In the present process, when applied to propane ammoxidation, a small amount of propylene is produced in relation to the unreacted propane in the effluent. Thus the propane effluent containing propylene in the amount of up to 8 mole percent, but usually no more than 6 mole percent, of the amount of propane plus propylene can comprise substrate feed to the present process.

And in general the C$_3$ to C$_5$ alkane feed to the reaction zone of the process of the present invention can contain one or more C$_3$ to C$_5$ olefins. The C$_3$ to C$_5$ olefin content of the feed to the present ammoxidation process can contain from zero to 8 mole percent of such olefin(s), based on the moles of C$_3$ to C$_5$ paraffin plus olefins fed, and this feed can be from any source. However, larger amounts of C$_3$ to C$_5$ olefins may be present in the substrate paraffin feed, but the usual proportions are as stated, and the usual olefin is that corresponding to the particular paraffin fed to the reaction zone of the present ammoxidation process.

Examples of diluents useful in the reaction zone are N$_2$, He, CO$_2$, H$_2$O and Ar. The unreacted excess paraffin, such as propane, over the stoichiometric amount of O$_2$ and NH$_3$ acts, of course, as a diluent or further diluent. The excess paraffin as recited in the claims is an important feature of the invention.

The reaction temperature range can vary from 350° to 700°, but is usually 440° to 550° C. The latter temperature range is especially useful in the case of propane ammoxidation to acrylonitrile.

The average contact time can often be from 0.01 to 10 seconds, but is usually from 0.02 to 10 seconds, more usually from 0.05 to 5 seconds.

The pressure of the reaction usually ranges from 1 to 45 psig. Most often, pressure is somewhat above atmospheric, i.e. 1 to 15 psi.

In any event, the pressure, temperature and contact times are not the essence of the invention and can be outside these ranges. The most advantageous combination of these conditions for a given desired result from a given feed can be determined by routine experimentation.

The nitrile products of the present process contain one C to C double bond and one nitrile group. The desired olefin products contain one double bond and the same number of C atoms as the paraffin feed.

The catalysts of the inventions contain the elements indicated by the empirical formula 1 in the relative atomic proportions indicated by such formula, as already noted. They can be used in unsupported form or with suitable carriers such as silica, alumina, zirconia or mixtures thereof. In specific examples herein where $SiO_2$ or alumina are present, they are such carriers.

The following examples of the invention are exemplary and should not be taken as in any way limiting.

COMPARATIVE CATALYST EXAMPLE A 54.66 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.96 g of $Cu(NO_3)_2.2.5H_2O$, 1.02 g of ammonium meta tungstate, 3.59 g of $TeO_2$, 1.32 g of $(NH_4)_6Mo_7O_{24}.4H_2O$, and 66.66 g $Fe(NO_3)_3.9H_2O$ were combined in about 100 ml of water and stirred for about one hour with moderate heating. This mixture was then added to the slurried filter cake. To this was added 1.75 g of $NH_4VO_3$ dissolved in 150 ml of water. 53.37 g of 40 wt % $SiO_2$ sol were then added. The mixture was evaporated to near-dryness on a hot plate with constant stirring. It was then dried at 120° C. for 16 hours. The dried material was heat treated in air at 290° C. for 3 hours and at 425° C. for 3 hours then ground and screened to collect the 20-35 mesh size particles. These particles were further heat treated in air at 810° C. for three hours. In this example tin was absent.

COMPARATIVE CATALYST EXAMPLE B 78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 16.51 g of 40 wt % $SiO_2$ sol and 135.62 g of 20 wt % $SnO_2$ sol were then added. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. 5 g of the resulting material were placed in a 25 ml flask and 6 ml of water were added drop-wise in such a manner as to uniformly wet the particles. The particles were then dried at 120° C. The dried particles were then heat treated in air at 290° C. for 3 hours and then at 810° C. for 30 minutes. This catalyst contained no vanadium.

COMPARATIVE CATALYST EXAMPLE C 78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 16.51 g of 40 wt % $SiO_2$ sol and 135.62 g of 20 wt % $SnO_2$ sol were then added. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. 5 g of the resulting material were placed in a 25 ml flask and 6 ml of an oxalic acid solution of $NH_4VO_3$ (0.00388 g $NH_4VO_3$/ml of solution) were added drop-wise in such a manner as to uniformly wet the particles. The particles were then dried at 120° C. The dried particles were then heat treated in air at 290° C. for 3 hours and then at 810° C. for 30 minutes. The atomic ratio of Sb:V was 102.9.

CATALYST EXAMPLE 1

78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 16.51 g of 40 wt % $SiO_2$ sol and 135.62 g of 20 wt % $SnO_2$ sol were then added. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. 5 g of the resulting material were placed in a 25 ml flask and 6 ml of an oxalic acid solution of $NH_4VO_3$ (0.00388 g $NH_4VO_3$/ml of solution) were added drop-wise in such a manner as to uniformly wet the particles. The particles were then dried at 120° C. The resulting dried particles were again placed in a 25 ml flask and 6 ml of an oxalic acid solution of $NH_4VO_3$ (0.00388 g $NH_4VO_3$/ml of solution) were added drop-wise in such a manner as to uniformly wet the particles. The particles were then dried at 120° C. The dried particles were then heat treated in air at 290° C. for 3 hours and then at 810° C. for 30 minutes. The atomic ratio of Sb:V was 51.4.

CATALYST EXAMPLE 2

78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 16.51 g of 40 wt % $SiO_2$ sol and 135.62 g of 20 wt % $SnO_2$ sol were then added. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. 5 g of the resulting material were placed in a 25 ml flask and 6 ml of an oxalic acid solution of $NH_4VO_3$ (0.00388 g $NH_4VO_3$/ml of solution) were added drop-wise in such a manner as to uniformly wet the particles. The particles were then dried at 120° C. The resulting dried particles were again placed in a 25 ml flask and 6 ml of an oxalic acid solution of $NH_4VO_3$ (0.00388 g $NH_4VO_3$/ml of solution) were added drop-wise in such a manner as to uniformly wet the particles. The particles were then dried at 120° C. The resulting dried particles were placed for a final time in a 25 ml flask and 6 ml of an oxalic acid solution of $NH_4VO_3$ (0.00388 g $NH_4VO_3$/ml of solution) were added drop-wise in such a manner as to uniformly wet the particles. The particles were then dried at 120° C. The dried particles were then heat treated in air at 290° C. for 3 hours and then at 810° C. for 30 minutes. The atomic ratio of Sb:V was 34.3.

COMPARATIVE CATALYST EXAMPLE D 78.71 g of $Sb_2O_3$ were slurried in a mixture of 200 ml of water and 300 ml of concentrated reagent grade nitric acid solution. The slurry was refluxed with constant stirring for 3 hours. It was then cooled to room temperature and filtered. The filter cake was washed once with water and filtered again. The resulting filter cake was then slurried in about 100 ml of water. 1.75 g of $NH_4VO_3$ and 2.86 g of ammonium meta tungstate were dissolved together in 200 ml of water and then added to the slurried filter cake. To this mixture was added 13.26 g of $Cu(NO_3)_2.2.5H_2O$ dissolved in 100 ml water along with 4.07 g of $TeO_2$. 65.93 g of 40 wt % $SiO_2$ sol and 149.66 g of 9.61 wt % $TiO_2$ sol were then added. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. A portion of these particles were further heat treated in air at 810° C. for three hours. In this example tin was absent.

COMPARATIVE CATALYST EXAMPLE E 78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 78.44 g of 40 wt % $SiO_2$ sol and 135.62 g of 20 wt % $SnO_2$ sol were then added. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. This composition contained no vanadium.

CATALYST EXAMPLE 3

78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 78.44 g of 40 wt % $SiO_2$ sol and 135.62 g of 20 wt % $SnO_2$ sol were then added along with 1.75 g of $NH_4VO_3$ dissolved in 500 ml of water. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. The atomic ratio of Sb:V was 36.

CATALYST EXAMPLE 4

78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 78.44 g of 40 wt % $SiO_2$ sol and 135.62 g of 20 wt % $SnO_2$ sol were then added along with 1.75 g of $NH_4VO_3$ dissolved in 500 ml of water. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. 5 g of the resulting material were placed in a 25 ml flask and 6 ml of an oxalic acid solution of $NH_4VO_3$ (0.00388 g $NH_4VO_3$/ml of solution) were added drop-wise in such a manner as to uniformly wet the particles. The particles were then dried at 120° C. The dried particles were then heat treated in air at 290° C. for 3 hours and then at 810° C. for 30 minutes. The atomic ratio of Sb:V was 25.

CATALYST EXAMPLE 5

78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 78.44 g of 40 wt % $SiO_2$ sol and 135.62 g of 20 wt % $SnO_2$ sol were then added along with 1.75 g of $NH_4VO_3$ dissolved in 500 ml of water. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. 5 g of the resulting material were placed in a 25 ml flask and 6 ml of water were added drop-wise in such a manner as to uniformly wet the particles. The particles were then dried at 120° C. The dried particles were then heat treated in air at 290° C. for 3 hours and then at 810° C. for 30 minutes. The atomic ratio of Sb:V was 36.

COMPARATIVE CATALYST EXAMPLE F 78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 78.44 g of 40 wt % $SiO_2$ sol and 135.62 g of 20 wt % $SnO_2$ sol were then added along with 0.18 g of $NH_4VO_3$ dissolved in 500 ml of water. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. The atomic ratio of antimony to vanadium was 360.

CATALYST EXAMPLE 6

78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 78.44 g of 40 wt % $SiO_2$ sol and 135.62 g of 20 wt % $SnO_2$ sol were then added along with 3.51 g of $NH_4VO_3$ dissolved in 500 ml of water. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. The atomic ratio of Sb:V was 18.

CATALYST EXAMPLE 7

78.71 g of $Sb_2O_3$ were slurried in a mixture of 200 ml of water and 300 ml of concentrated reagent grade nitric acid solution. The slurry was refluxed with constant stirring for 3 hours. It was then cooled to room temperature and filtered. The filter cake was washed once with water and filtered again. The resulting filter cake was then slurried in about 100 ml of water. 1.75 g of $NH_4VO_3$ and 2.86 g of ammonium meta tungstate were dissolved together in 200 ml of water and then added to the slurried filter cake. To this mixture was added 13.26 g of $Cu(NO_3)_2.2.5H_2O$ dissolved in 100 ml water along with 4.07 g of $TeO_2$. 36.95 g of 40 wt % $SiO_2$ sol, 135.63 g of 20 wt % $SnO_2$ sol, and 73.90 g of 20 wt % alumina sol were then added. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. A portion of these particles were further heat treated in air at 810° C. for three hours. The atomic ratio of Sb:V was 36. The support was silica-alumina.

CATALYST EXAMPLE 8

78.71 g of $Sb_2O_3$ were slurried in a mixture of 200 ml of water and 300 ml of concentrated reagent grade nitric acid solution. The slurry was refluxed with constant stirring for 2 hours. It was then cooled to room temperature and filtered. The filter cake was washed once with water and filtered again. The resulting filter cake was then slurried in about 100 ml of water. 13.26 g of $Cu(NO_3)_2.2.5H_2O$, 2.86 g of ammonium meta tungstate, and 4.07 g of $TeO_2$ were combined in about 100 ml of water and stirred for about one hour with moderate heating. This mixture was then added to the slurried filter cake. 78.44 g of 40 wt % $SiO_2$ sol and 135.62 g of 20 wt % $SnO_2$ sol were then added along with 0.88 g of $NH_4VO_3$ dissolved in 500 ml of water. The mixture was evaporated to near-dryness on a hot plate with constant stirring. It was then dried at 120° C. for 16 hours. The dried material was heat treated in air at 425° C. for 3 hours then ground and screened to collect the 20-35 mesh size particles. These particles were further heat treated in air at 810° C. for three hours. The atomic ratio of Sb:V was 72.

In the following ammoxidation examples summarized in Table 1, the catalyst is in a tubular ⅜ inch I.D. titanium fixed bed reactor. Pressure was slightly above atmospheric. The reactor is equipped with a preheat leg and is immersed in a temperature controlled molten salt bath. The feed is fed to the catalyst for at least one hour before collection of product; the runs of each example last 30-60 minutes during which the product is collected for analysis.

In these specific examples the reactor temperature was 460° F. and the mole ratios in the feed to the reaction zone were 5 propane/0.8 NH$_3$/2 O$_2$/1 H$_2$O As will be evident to those skilled in the art, various modifications of this invention can be made or followed in the light of the foregoing disclosure and discussion without departing from the spirit and scope of the disclosure or from the scope of the claims.

in the relative atomic proportions indicated by the subscripts, where
A is selected from Te and Bi
D is one or more optional elements selected from Mo, W, Ti, Ge, Ce, La, Cr, Mn, Mg, Ca, Co, Ni, Fe, Nb, Ta, Ag, Zn, Cd, B, P, Na, K and Cs, and
a is 0.001 to 30
d is zero to 30
c is 0.001 to 30
m is 0.1 to 60

TABLE 1

| Ammoxidation Example No. | Catalyst Example No. | Mole Ratio Sb:V | CT Secs | Percent Propane Conversion | Propane: Mole % Conversion to | | | | | |
|---|---|---|---|---|---|---|---|---|---|---|
| | | | | | AN | HCN | AN + HCN | C$_3$= | AN + C$_3$= | AN + HCN + C$_3$= |
| A | A | 25 | 3.2 | 4.9 | 0.2 | 0.1 | | 0.6 | | |
| B | B | No V | 3.8 | 1.8 | 1.0 | 0.1 | | 0.0 | | |
| C | C | 102.9 | 3.2 | 7.3 | 4.0 | 0.2 | 4.2 | 0.6 | 4.6 | 4.8 |
| 1 | 1 | 51.4 | 3.2 | 8.8 | 4.9 | 0.5 | 5.4 | 0.6 | 5.5 | 6.0 |
| 2 | 2 | 34.3 | 3.2 | 9.7 | 5.0 | 0.5 | 5.5 | 0.7 | 5.7 | 6.2 |
| D | D | 36 | 3.3 | 4.8 | 0.4 | 0.0 | | 0.3 | | |
| E | E | No V | 2.9 | 1.5 | 0.9 | 0.1 | | 0.0 | | |
| 3 | 3 | 36 | 3.4 | 12.4 | 6.8 | 1.2 | 8.0 | 0.7 | 7.5 | 8.7 |
| 4 | 4 | 25 | 3.5 | 13.1 | 6.5 | 0.4 | 6.9 | 0.9 | 7.1 | 7.8 |
| 5 | 5 | 36 | 3.3 | 12.9 | 7.3 | 1.3 | 8.6 | 0.6 | 7.9 | 9.2 |
| F | F | 360 | 2.6 | 3.3 | 1.8 | 0.1 | | 0.3 | | |
| 6 | 6 | 18 | 3.5 | 13.5 | 6.2 | 0.7 | 6.9 | 1.4 | 7.6 | 8.3 |
| 7 | 7 | 36 | 3.6 | 10.3 | 4.8 | 0.2 | 5.0 | 0.6 | 5.4 | 5.6 |
| 8 | 8 | 72 | 3.2 | 7.8 | 4.5 | 0.9 | 5.4 | 0.3 | 4.8 | 5.7 |

CT = contact time
C$_3$= = propylene
AN = acrylonitrile

What we claim is:

1. A metal-oxide catalyst containing the elements indicated by the empirical formula, $V_v A_a D_d Sn_m Sb_n Cu_c O_x$ n is 0.1 to 60
n/v is >12 and <100
m+n is ≦v+a+c+d, and
x is determined by the valence requirements of the elements present.

* * * * *

UNITED STATES PATENT AND TRADEMARK OFFICE
CERTIFICATE OF CORRECTION

PATENT NO. : 5,079,207
DATED : January 7, 1992
INVENTOR(S) : Brazdil et al

It is certified that error appears in the above-indentified patent and that said Letters Patent is hereby corrected as shown below:

Claim 1, line 34, column 10, change "$\leq$" to read ... $\geq$ ...

Signed and Sealed this

Twenty-second Day of June, 1993

Attest:

MICHAEL K. KIRK

Attesting Officer     Acting Commissioner of Patents and Trademarks